US00PP15093P3

(12) United States Plant Patent
Evison et al.

(10) Patent No.: US PP15,093 P2
(45) Date of Patent: Aug. 24, 2004

(54) CLEMATIS PLANT NAMED 'EVIRIDA'

(50) Latin Name: *Clematis florida*
Varietal Denomination: EVIrida

(76) Inventors: Raymond J. Evison, Domarie Vineries, St. Sampsons CI GY2 4AF (GB); Mogens Olesen, Hillerodvejen 49, Fredensborg (DK), DK3480

( * ) Notice: Subject to any disclaimer, the term of this patent is extended or adjusted under 35 U.S.C. 154(b) by 237 days.

(21) Appl. No.: 09/863,123

(22) Filed: May 22, 2001

(65) Prior Publication Data

US 2003/0074704 P1 Apr. 17, 2003

(51) Int. Cl.[7] ..... A01H 5/00
(52) U.S. Cl. ..... Plt./228
(58) Field of Search ..... Plt./228

(56) References Cited

PUBLICATIONS

Community Plant Variety Office. "Certificate on the Grant of Community Plant Variety Rights" Oct. 25, 1999. 6 pages. EU.

GTITM UPOVROM Citation for 'EVIrida' as per QZ PBR 970412; Mar. 26, 1997.*

GTITM UPOVROM Citation for 'EVIrida' as per GB BIL 02300205.*

* cited by examiner

*Primary Examiner*—Kent Bell

(57) ABSTRACT

A new evergreen Clematis cultivar which has long continuous flowering season over which it produces attractive white flowers with a hint of green and a green center. This new and distinct variety has shown to be uniform and stable in the resulting generations from asexual propagation.

1 Drawing Sheet

SUMMARY OF THE DISCOVERY

Classification:

Botanical: *Clematis florida* 'EVIrida'.

Commercial: Double flowered compact cultivar.

The present discovery constitutes a new and distinct variety of Clematis which was discovered in a cultivated area. The new variety of Clematis was a naturally occurring mutation of unknown causation discovered growing within a planting of Clematis plant of the species *'florida'* (not patented.). The resulting mutation was evaluated and asexually propagated in a controlled environment. The new variety is named 'EVIrida'.

The clematis plant of the present discovery has a unique combination of characteristics which are outstanding in the new variety and which distinguish it from the parental *Clematis, florida*. The unique qualities that this variety has:

1. An attractive flat flower form with an open center.
2. Broad, slight overlapping tepals giving the flower a full form.
3. Flower has a prominent, central tuft of green, sterile styles.
4. Continuous flowering period, from May to October.

This combination of qualities was lacking in clematis varieties known to us that were in commercial cultivation and the qualities have been substantially achieved in the new variety.

'EVIrida' was selected by Raymond J. Evison and Mogens N. Olesen in their Clematis development program in Domarie Vineries Les Sauvagees, St. Sampsons, Guernsey, Channel Islands, United Kingdom in 1993. Asexual reproduction of 'EVIrida' by cuttings was first done by Raymond J. Evison in Domarie Vineries Les Sauvagees, St. Sampsons, Guernsey, Channel Islands, United Kingdom in 1993. This initial and subsequent propagations have demonstrated that the characteristics of 'EVIrida' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers and leaves of the new variety, with different flowers shown in various stages of maturity. The flower form, flower colors, flower buds, floral parts, flower pedicels and the cultivar's foliage are depicted. Specifically illustrated in Sheet 1:

1. Stem showing branching and the attachment of leaves, nodes, and a bud;
2. Pedicel, leaves, and open flower.
3. Open flower, upper surface;
4. Open flower, lower surface;
5. Tepals;
6. Pedicel flower;
7. Petiolule and leaflets.

DETAILED DESCRIPTION OF THE VARIETY

The following is a detailed description of 'EVIrida', as observed in its growth throughout the flowering period in glasshouses at Domarie Vineries Les Sauvagees, St. Sampsons, Guernsey, Channel Islands, United Kingdom. The observed plants were 2 years old, grown by vegetative propagation in 2 liter pots. Certain phenotypical characteristics of the variety may vary under different environmental, cultural, agronomic, seasonal, and climatic conditions. Color references are made using The Royal Horticultural Society (London, England) Colour Chart, 1995, except where common terms of color are used. For a comparison, the nearest existing Clematis variety is the species *C. florida*. Chart 1 details the physical characteristics of the applicant variety and the comparison variety.

CHART 1

| | 'EVIrida' | *C. florida* |
|---|---|---|
| Filaments | Long, white. | Short, purple. |
| Center form | Very open, filaments held horizontally. | Compact, closed. |
| Center color | Green (exposed styles.) | Dark purple (Anthers, stigmas.) |
| Tepal Recurvature | Flat. | Recurved. |

Parent: Mutation of *Clematis florida.*

FLOWER AND FLOWER BUD

Blooming habit: Continuous.

Flower bud:

*Size.*—20–30 mm in length.

*Bud form.*—Elliptical.

*Bud color.*—Petals: Outer surface is Yellow-Green Group 145B at ¼ opening. Sepals: Upper surfaces are Yellow-Green Group 144B in middle and basal zones, Yellow-Green Group 149D at margins. Lower surfaces are Yellow-Green Group 149D.

*Peduncle.*—Surface: Smooth. Length: 90–120 mm average length. Color: Medium green. Green Group 143C. Strength: Horizontal.

*Borne.*—Singly.

Flower bloom:

*Size.*—Medium. 90 mm in diameter, 15 mm in height.

*Form.*—Flat. Completely open, outer tepals are flat.

*Color.*—Upon opening, the upper surface is Yellow-Green Group 149D at base, margin, and interior. Upon opening, the reverse side is Yellow-Green Group 149D, with a central streak running the length of the tepal, Yellow-Green Group 144B. After opening, the upper surface is White Group 157D at base, margin, and interior. After opening, the reverse surface is White Group 157D, with a central streak running the length of the tepal, Yellow-Green Group 149D. The general tonality of the open flower is White Group 157D.

*Fragrance.*—None.

*Lasting quality on plant.*—21 to 28 days on plant; 2 to 5 days as a cut flower.

Tepals:

*Quantity.*—Single. Average quantity: 6.

*Shape.*—Individual tepal shape is elliptical.

*Cross section.*—Flat.

*Margin.*—Entire. Undulated, with one to two wave crests on each tepal edge.

*Tepal apex.*—Narrowly acute.

*Recurvature of tip.*—None.

*Persistence.*—Outer tepals drop off cleanly.

*Arrangement.*—Tepals are arranged regularly.

Reproductive organs: The plant is sterile in that it exhibits no anthers or filaments but has a center of approximately 50 sterile styles.

*Pollen.*—None.

*Anthers.*—None.

*Filaments.*—None.

*Stigmas.*—None.

*Styles.*—Color: Yellow-Green Group 143D. Quantity: Typically 50.

*Ovaries.*—None.

PLANT

Plant form: Climbing and spreading.

Plant growth: Moderately vigorous. In the observed situation, the observed plant spread was less than 40 cm.

Height: When trellised, one seasons growth attains 2.0–3.0 meters.

Hardiness: Trials to date show the variety hardy in USDA zones 6–9.

Stems:

*Length.*—200 cm.

Color: Young wood: Green Group 137C, with intonations of Greyed-Purple Group 187A. Older wood: Greyed-Orange Group 165C.

*Internodes.*—Cylindrical in cross section. The length between nodes of the vegetative growing shoot is 130–180 mm.

*Petioles.*—Size: Average length: Petiolus=30–60 mm. Petiolule=0–10 mm. Color: Green Group 137C. Clasping: Clasps by leaf petiolus. Underneath: Without prickles.

*Bark.*—Young wood: Smooth. Older wood: Smooth.

Plant foliage: Evergreen. Varies between: a) Trifoliate; b) 3 trifoliate leaflets arranged in trifoliate form; c) 5 leaflets arranged in pinnate form.

*Leaf size.*—Entire leaf size is typically 120 mm long and 90 mm wide. Leaflets are typically 35 mm long 20 wide.

*Abundance.*—Average.

*Color.*—Top: Green Group 137A. Bottom: Green Group 137C. New growth: Internodes green; foliage green. Older growth: Internodes dark green, turning brown. Foliage dark green.

Plant leaves and leaflets:

*Stipules.*—Absent.

*Leaf edge.*—Terminal leaflet margin is normally entire but sometimes undulated and/or with rounded lobes.

*Shape.*—Overall shape is lanceolate with an acute tip and a rounded-acute base.

*Texture.*—Thin. Upper side: Glabrous. Lower side: Ribbed.

*Surface.*—Matte Finish.

Disease resistance: Subject to any disease which normally attacks the species.

Additional information: After tepals drop off stamens fold back completely, revealing green, central tuft of sterile styles, some of which by this stage have a miniature petaloid-stamen-like appearance. This is unique — no other clematis known to us displays this trait.

We claim:

1. A new and distinct variety of Clematis plant, substantially as herein illustrated and described, as a distinct and novel Clematis variety due to its abundant white flowers, excellent flower longevity, long recurrent flowering period from early summer through autumn, and compact growth making it suitable for nursery production in containers.

* * * * *

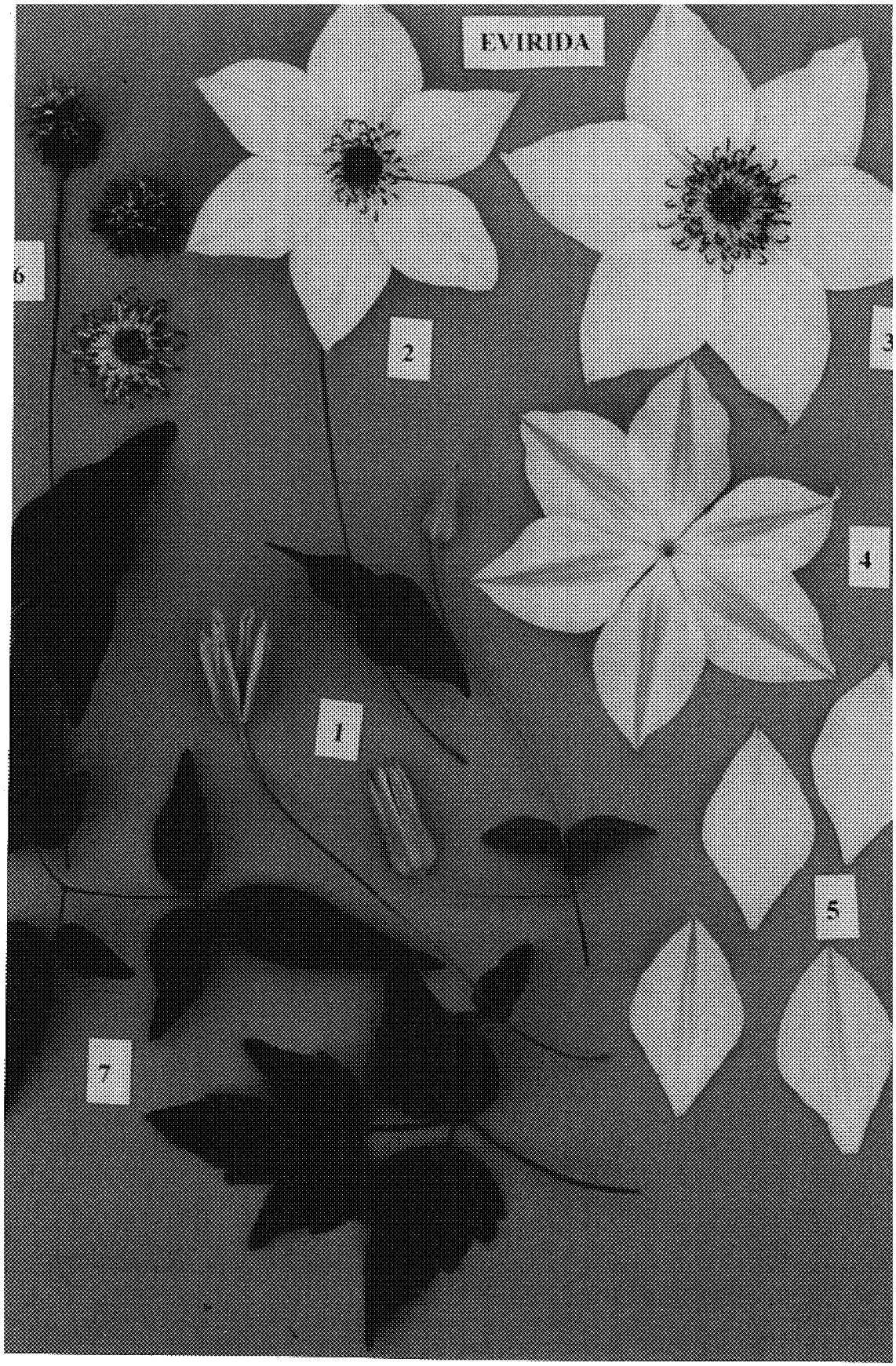
EVIRIDA
6
2
3
4
1
5
7